(12) United States Patent
Bossaert et al.

(10) Patent No.: US 9,981,929 B2
(45) Date of Patent: May 29, 2018

(54) METHOD FOR PREVENTION OF PREMATURE POLYMERIZATION

(71) Applicant: NITTO BELGIUM NV, Genk (BE)

(72) Inventors: Greet Bossaert, Genk (BE); Monica Gomes, Genk (BE); Bart Forier, Genk (BE)

(73) Assignee: NITTO BELGIUM NV, Genk (BE)

( * ) Notice: Subject to any disclaimer, the term of this patent is extended or adjusted under 35 U.S.C. 154(b) by 0 days. days.

(21) Appl. No.: 15/700,773

(22) Filed: Sep. 11, 2017

(65) Prior Publication Data

US 2017/0369458 A1    Dec. 28, 2017

Related U.S. Application Data

(62) Division of application No. 15/079,967, filed on Mar. 24, 2016, now Pat. No. 9,796,693.

(30) Foreign Application Priority Data

Mar. 26, 2015  (EP) .................................... 15000894

(51) Int. Cl.

| C07D 279/20 | (2006.01) |
|---|---|
| C09B 49/06 | (2006.01) |
| C07C 67/62 | (2006.01) |
| C09B 17/00 | (2006.01) |
| C09B 19/00 | (2006.01) |
| C09B 21/00 | (2006.01) |
| C07D 279/18 | (2006.01) |
| C07C 67/03 | (2006.01) |
| C08L 33/08 | (2006.01) |
| C08F 220/18 | (2006.01) |

(52) U.S. Cl.
CPC ............ *C07D 279/20* (2013.01); *C07C 67/03* (2013.01); *C07C 67/62* (2013.01); *C07D 279/18* (2013.01); *C08F 220/18* (2013.01); *C08L 33/08* (2013.01); *C09B 17/00* (2013.01); *C09B 19/00* (2013.01); *C09B 21/00* (2013.01); *C09B 49/06* (2013.01); *C08G 2261/58* (2013.01)

(58) Field of Classification Search
CPC ........ C07D 279/20; C07B 49/06; C07C 67/62

USPC .......................................................... 544/37
See application file for complete search history.

(56) References Cited

U.S. PATENT DOCUMENTS

| 6,458,989 B1 | 10/2002 | Aichinger et al. |
|---|---|---|
| 2006/0074257 A1 | 4/2006 | Bass et al. |
| 2007/0116757 A1 | 5/2007 | Rariy et al. |

FOREIGN PATENT DOCUMENTS

| DE | 29 13 218 A1 | 10/1980 |
|---|---|---|
| EP | 2 017 293 A1 | 1/2009 |
| JP | S50-117716 A | 9/1975 |
| JP | 2000-016966 A | 1/2000 |
| JP | 2002-509904 A | 4/2002 |
| JP | 2006-131894 A | 5/2006 |
| JP | 2013-018963 A | 1/2013 |
| JP | 2014-005372 A | 1/2014 |

OTHER PUBLICATIONS

Extended European Search Report issued in Patent Application No. EP 15000894.4 dated Aug. 10, 2015.
Notification of Reasons for Refusal issued by the Japanese Patent Office dated Mar. 23, 2017 in connection with Japanese Patent Application No. 2016-061420.
Non-Final Office Action dated Feb. 16, 2017 in U.S. Appl. No. 15/079,967.
Notice of Allowance dated Jun. 14, 2017 in U.S. Appl. No. 15/079,967.
Notification of Reasons for Refusal issued by the Japanese Patent Office dated Nov. 16, 2017 in connection with Japanese Patent Application No. 2016-061420.

*Primary Examiner* — Kahsay Habte
(74) *Attorney, Agent, or Firm* — Jean C. Edwards, Esq.; Edwards Neils LLC

(57) ABSTRACT

The present invention relates to a method for prevention of premature polymerization during the preparation, purification, transportation and storage of a polymerizable compound with at least one conjugated unsaturated group in the presence of an azine dye-based compound as inhibitor. Further the present invention relates to methods of preparing such inhibitors as well as to the inhibitors itself, as well as to methods of improving solubility and stability of dissolved inhibitors.

7 Claims, 1 Drawing Sheet
(1 of 1 Drawing Sheet(s) Filed in Color)

Figure 1: Azine dye-based compound I-2a in SMA (left vial) and MB in SMA (right vial) after treatment with MeOH
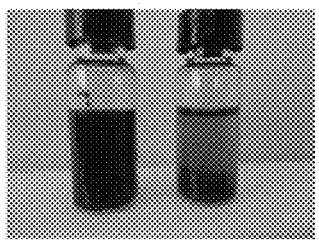
Figure 2: Azine dye-based compound I-4 in SMA before (left vial) and after (right vial) treatment with MeOH
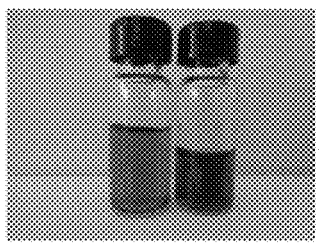
Figure 3: Transesterification reaction of methyl methacrylate to SMA
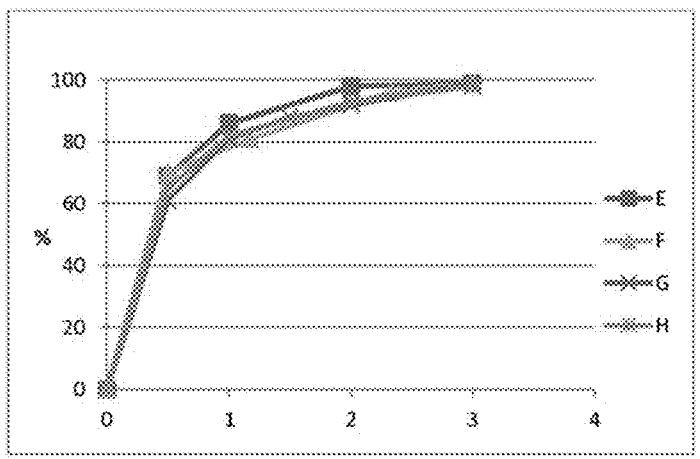

METHOD FOR PREVENTION OF PREMATURE POLYMERIZATION

CROSS-REFERENCE TO RELATED APPLICATIONS

The present application is a divisional patent application of U.S. patent application Ser. No.: 15/079,967, filed Mar. 24, 2016, which claims priority from European Patent Application No. 15000894.4, filed Mar. 26, 2015, the contents of all of which are herein incorporated by reference in their entirety.

The present invention relates to a method for prevention of premature polymerization during the preparation, purification, transportation and storage of a polymerizable compound with at least one conjugated unsaturated group in the presence of an azine dye-based compound as inhibitor. Further the present invention relates to methods of preparing such inhibitors as well as to the inhibitors itself, as well as to methods of improving solubility and stability of dissolved inhibitors.

BACKGROUND OF THE INVENTION

Polymerizable compounds with at least one conjugated unsaturated group are widely used as basic chemicals. Examples are acrylic monomers, in particular acrylic acid and methacrylic acid as well as their esters. They are mostly used for the synthesis of polymers.

These polymerizable compounds, while being valuable starting materials for the preparation of a broad variety of synthetic materials, suffer from the drawback of their inherent activity, i.e. the fact that they are viable to undergo polymerization even at times where polymerization is not desired. Examples of such undesired polymerizations, which accordingly require inhibition, are purification processes, often involving high temperatures (such as distillation processes) as well as the synthesis of such starting materials, as already during synthesis a premature polymerization needs to be prevented in order to maintain high yield and efficiency of the synthetic procedure.

In the art there are already examples of inhibitors which may be employed under these circumstances.

For example, U.S. Pat. No. 2,715,101 A discloses the use of methylene blue (MB) for the stabilization of diacetylene or of mixtures containing diacetylene against polymerization. However, methylene blue has low solubility in a polymerizable compound with at least one conjugated unsaturated group, like acrylic acid or methacrylic acid or their esters.

A similar disclosure is given in EP 2053066 A1 as well as in U.S. Pat. No. 4,983,761.

MB, due to the presence of the chloride anion furthermore has proven to be corrosive. In order to reduce the content of this corrosive component, US 2006074257 A1 suggests replacing the chloride anion with other anionic groups, such as sulfates or acetates using for example ion exchange processes. However, those types of methylene blue derivatives have still low solubility. In addition, these compounds require a separate synthesis step including isolation steps, rendering the overall process of stabilizing the polymerizable compounds against premature polymerization laborious.

OBJECT OF THE PRESENT INVENTION

Accordingly, it is the object of the present invention to overcome at least one of the drawbacks mentioned above, and to provide a method to prevent a premature polymerization of a polymerizable compound with at least one conjugated unsaturated group. Preferably the process should be as simple as possible to avoid separate handling and isolation steps, while ensuring the desired goal of preventing polymerization. A further object of the present invention is to provide new stabilizers (inhibitors) suitable to prevent the polymerization of polymerizable compounds with at least one conjugated unsaturated group, which has good solubility in a polymerizable compound.

It is in particular an object of the present invention to provide methods as well as inhibitors useful for these methods, allowing the purification of existing monomeric polymerizable compounds, in particular by distillation, as well as methods and inhibitors useful for the preparation of such monomeric polymerizable compounds, in particular by transesterification.

SUMMARY OF THE INVENTION

This object is solved with the subject matter as outlined in the claims as well as in the description. In one aspect, the present invention provides a method of preventing premature polymerization of a polymerizable compound by generating in situ an organic sulfonate salt of an azine compound (also designated azine dye based compound), for example during the purification or the preparation of the polymerizable compound. In a further aspect, the present invention provides novel inhibitors which are azine based compounds, comprising an azine cation associated with an organic sulfonate anion. In addition, the present invention provides methods for improving the stability of inhibitors described herein.

As will be clear for the skilled reader, in the following the present invention provides methods for inhibiting the undesired polymerization of polymerizable compounds, in particular during purification processes, including distillation processes, as well as manufacturing methods, in particular transesterification reactions, wherein the inhibitory activity is provided by means of inhibitors formed in situ during the respective processing steps or manufacturing steps, or wherein the inhibitor is prepared prior to its use in the methods disclosed herein. The present invention also provides novel inhibitory compounds as outlined in the following.

DEFINITIONS

By "inhibitor" or "stabilizer" a compound which prevents a premature polymerization during the preparation, purification, transportation and storage of a polymerizable compound with at least one conjugated unsaturated group is meant.

By "conjugated unsaturated group" the alternation of carbon-carbon, carbon-heteroatom or heteroatom-heteroatom multiple bonds with single bonds is meant. Examples include conjugated dienes as well as acrylates.

By "polymerizable compound" is meant that said compound can undergo a polymerization reaction. The type of polymerization is not limited, i.e. may be radical, anionic, cationic, etc.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1: Azine dye-based compound I-2a in stearyl methacrylate (SMA) (left vial) and MB in SMA (right vial) after treatment with MeOH.

FIG. 2: Azine dye-based compound I-4 in SMA before (left vial) and after (right vial) treatment with MeOH.

FIG. 3: Kinetic profiles of Transesterification reactions of methyl methacrylate to SMA.

DETAILED DESCRIPTION OF THE INVENTION

As outlined above, in one aspect of the present invention the desired inhibitory activity of an azine based inhibitor is generated by preparing an organic sulfonate salt of an azine based compound in situ, by providing a mixture of an azine compound, such as MB, with an organic sulfonate salt, such as an alkali salt, in the presence of the polymerizable compound or a reaction mixture to produce the polymerizable compound and then carrying out the desired reaction, such as purification by distillation or synthesis of the polymerizable compound, for example by transesterification of a (meth)acrylate or ester thereof with an alcohol. Thereby it is not required to synthesize and isolate the inhibitor before addition to the polymerizable compound. Surprisingly, it has been found that it is entirely sufficient to carry out the synthesis of the desired inhibitor in situ so that the overall process of preventing premature polymerization of a polymerizable compound is rendered less complex. By providing the two components of the desired inhibitor, i.e. the azine based compound (defined more precisely below) as well as the sulfonate component (defined more precisely below), it is possible to generate the inhibitor in situ using the temperature raise usually applied when starting either a synthetic process for preparing a polymerizable compound or the distillation process for purification purposes. It has been found that the reaction between the two components takes easily place during such initial stages of synthetic procedures or purification processes, yielding the desired inhibitor (i.e. the sulfonate salt of the azine compound) while the generation of the by-product, such as an alkali halogenide salt (such as NaCl in case of using as starting components MB and a sodium sulfonate), does not have any detrimental effect on the inhibitory action.

In accordance with the present invention, it is also considered to employ mixtures of inhibitors, i.e. it is possible to employ different azine dye-based compounds and/or different sulfonate compounds in the same process. One potential advantage of such a use of different components, yielding different inhibitors, is the fact that it is possible to tailor the inhibition profile with respect to the temperature profile of a given reaction and/or purification. In this respect, it is also possible to employ, in addition to an azine-based inhibitor, other types of polymerization inhibitors, in particular again to provide inhibitory activity at lower temperatures, as azine-based inhibitors tend to exhibit their inhibitory activity only at increased temperatures.

Accordingly, in one aspect of the present invention, the inhibitory action during a desired reaction and/or purification step is provided by the in situ formation of a soluble inhibitor, enabling the use of simple starting compounds, for example halogen salts of azine dye-based compounds and simple sulfonate salts. As outlined above, the method in accordance with the present invention enables to carry out the desired reaction and/or purification step without requiring a separate synthesis of the desired inhibitor being a sulfonate salt of an azine dye-based compound. In accordance with the present invention, it furthermore has been established that the formation of the salt resulting from the reaction of the sulfonate salt with the azine-based salt does not provide any negative influence on the reaction and/or purification step.

It has been confirmed that the azine dye-based compound generated in accordance with the in-situ generation process described herein has good solubility in a polymerizable compound and has the ability to prevent the polymerization of polymerizable compounds with at least one conjugated unsaturated group.

The azine dye-based compound has to be present in an amount sufficient to prevent polymerization, typically in concentrations of 1 to 5000 pm, such as 10 to 1000 ppm, preferably 20 to 700 ppm, and more preferably 100 to 500 ppm, relative to the polymerizable compound, in order to inhibit the polymerization of the polymerizable compound with at least one conjugated unsaturated group.

The azine dye-based compound as referred to herein comprises a cationic component and an anionic component.

In a particular embodiment of the present invention the azine dye-based compound employed in accordance with the present invention has the general formula:

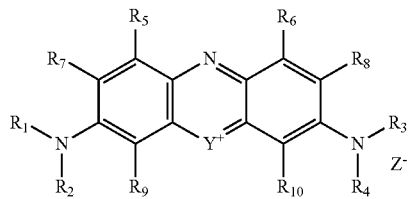

wherein:

Y is selected from the group consisting of S, O, or $NR^{11}$, preferably S, wherein $R^{11}$ is selected from the group consisting of hydrogen, an aliphatic moiety having from 1 to 20 carbon atoms, cycloalkyl, aryl, aralkyl, fluoroalkyl, fluoroaryl, fluoroaralkyl, chloro-alkyl, or chloroaryl, or chloroaralkyl having from 6 to 12 carbon atoms;

$R_1$-$R_4$ may be the same or different and each is selected from the group consisting of hydrogen, an aliphatic moiety having from 1 to 20 carbon atoms, cycloalkyl, aryl, aralkyl, fluoroalkyl, fluoroaryl, fluoroaralkyl chloroalkyl, chloroaryl, or chloroaralkyl having from 6 to 12 carbon atoms, heterocyclyl, any alkyl, alkylene, fluoroalkyl, fluoroalkylene chloroalkyl, or chloroalkylene chain being optionally interrupted by one or more hetero atoms. In addition, $R_1$ and $R_2$ together, or $R_3$ and $R_4$ together, may form part of an alicyclic or heterocyclic moiety having from 4 to 10 ring members;

$R_5$-$R_{10}$ may be the same or different and each is selected from the group consisting of hydrogen, an aliphatic moiety having from 1 to 20 carbon atoms, cycloalkyl, aryl, aralkyl, fluoroalkyl, fluoroaryl, fluoroaralkyl, chloroalkyl, chloroaryl, or chloroaralkyl having from 6 to 12 carbon atoms, heterocyclyl, any alkyl or alkylene fluoroalkyl, fluoroalkylene, chloroalkyl, or chloroalkylene chain being optionally interrupted by one or more hetero atoms. In addition, $R_5$ and $R_7$ together, or $R_6$ and $R_8$ together, or $R_1$ and $R_7$ together, or $R_2$ and $R_9$ together, or $R_3$ and $R_8$ together, or $R_{10}$ and $R_4$ together, may form part of an alicyclic or heterocyclic moiety having from 4 to 10 ring members;

$Z^-$ is any anion selected from the group consisting of $Cl^-$, $Br^-$, $I^-$ and F. Preferably the azine based compound is MB.

The organic sulfonate compound to be employed in the present invention may have the general formula $A^+ RSO_3^-$, wherein R is selected from the group consisting of an aliphatic moiety having from 1 to 30 carbon atoms, an aliphatic moiety having from 1 to 30 carbon atoms being substituted by cycloalkyl, aryl, aralkyl, fluoroalkyl, fluoroaryl, fluoroaralkyl, chloroalkyl, chloroaryl, or chloroaralkyl having from 6 to about 12 carbon atoms, heterocyclyl, any aliphatic moiety, alkyl or alkylene fluoroalkyl, fluoroalkylene, chloroalkyl, or chloroalkylene chain being optionally interrupted by one or more hetero atoms, R may also be selected among organic residues comprising a hydroxyl-substituted aromatic group, preferably phenyl, in particular 3-(2,5-di-tert-butyl-4-hydroxy-phenoxy)-propanyl (as outlined further below), $A^+$ is any cation selected from the group consisting of $Na^+$, $K^+$, $Li^+$ and $NH_4^+$.

In a particular embodiment R is selected from the group consisting of an aliphatic moiety having from 2 to 30 carbon atoms, an aliphatic moiety having from 2 to 30 carbon atoms being substituted by aralkyl, the aliphatic moiety being interrupted by one or more hetero atoms.

As far as aliphatic moieties having from 2 to 30 carbon atoms are mentioned, these aliphatic moieties may be straight chain or branched, preferably straight chain aliphatic moieties. Preferred ranges for carbon atom numbers of these aliphatic moieties are from 2 to 26, preferably from 6 to 24, in particular from 10 to 20, such as from 10 to 18, or 12 to 18.

In one embodiment R is selected from the group consisting of an aliphatic moiety having from 6 to 16 carbon atoms.

In another embodiment the sulfonate anion is selected from the group consisting of $R'—O—(CR^{12}_2)_n SO_3^-$, wherein n=1 to 5; preferably 2 to 4; wherein $R^{12}$ may be the same or different and each is selected from the group consisting of hydrogen, an aliphatic moiety having from 1 to 20 carbon atoms, cycloalkyl, aryl, aralkyl, fluoroalkyl, fluoroaryl, fluoroaralkyl, chloroalkyl, chloroaryl, or chloroaralkyl having from 6 to 12 carbon atoms;

R' is selected from the group consisting of an aliphatic moiety having from 1 to 20 carbon atoms, cycloalkyl, aryl, aralkyl, fluoroalkyl, fluoroaryl, fluoroaralkyl, chloroalkyl, chloroaryl, or chloroaralkyl having from 6 to 12 carbon atoms, heterocyclyl, any alkyl or alkylene fluoroalkyl, fluoroalkylene chloroalkyl, or chloroalkylene chain optionally being interrupted by one or more hetero atoms.

In a particular embodiment of the present invention, the sulfonate anion is selected from the group consisting of $CH_3(CH_2)_7SO_3^-$ (1-octanesulfonate), $CH_3(CH_2)_{15}SO_3^-$ (1-hexadecanesulfonate), $CH_3(CH_2)_{11}SO_3^-$ (1-dodecanesulfonate) and 3-(2,5-di-tert-butyl-4-hydroxy-phenoxy)-propane-1-sulfonate ($DBHQ(CH_2)_3SO_3^-$).

In a particular embodiment of the present invention, $R_1$-$R_4$ may be the same or different and each is selected from the group consisting of hydrogen, an aliphatic moiety having from 1 to 20 carbon atoms.

In another embodiment of the present invention, $R_1$-$R_4$ is methyl.

In a further embodiment of the present invention, $R_5$-$R_{10}$ may be the same or different and each is selected from the group consisting of hydrogen, an aliphatic moiety having from 1 to 20 carbon atoms.

In a further embodiment of the present invention, $R_5$-$R_{10}$ is hydrogen.

In a particular embodiment of the present invention, the inhibitor resulting from the reaction of the azine dye-based compound with the sulfonate has the formula I-1, I-2, or I-3:

In a particular embodiment of the present invention, the inhibitor resulting from the reaction of the azine dye-based compound with the sulfonate has the formula I-4:

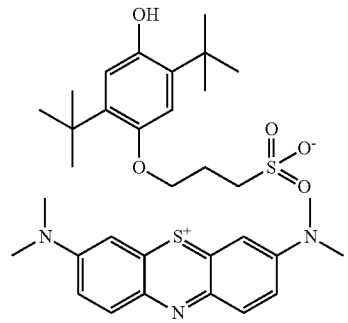

These azine dye-based compounds may be used alone, or with other compounds capable of inhibiting polymerization of a polymerizable compound with at least one conjugated unsaturated group. Such other inhibitor compounds may be water soluble, alcohol soluble, or soluble in organic solvents and include: hydroquinone (HQ); 4-methoxyphenol (MEHQ); 4-ethoxyphenol; 4-propoxyphenol; 4-butoxyphenol; 4-heptoxyphenol; hydroquinone monobenzylether; 1,2-dihydroxybenzene; 2-methoxyphenol; 2,5-dichlorohydroquinone; 2,5-di-tert-butylhydroquinone; acetylhydroquinone; hydroquinone monobenzoate; 1,4-dimercaptobenzene; 1,2-dimercaptobenzene; 2,3,5-trimethylhydroquinone; 4-aminophenol; 2-aminophenol; 2-N,N-dimethylaminophenol; 2-mercaptophenol; 4-mercaptophenol; catechol monobutylether; 4-ethylaminophenol; dihydroxyacetophenone; pyrogallol-1,2-dimethylether; methylthiophenol; t-butyl catechol; di-tert-butylnitroxide; di-tert-amylnitroxide; 2,2,6,6-tetramethyl-piperidinyloxy; 4-hydroxy-2,2,6,6-tetramethyl-piperidinyloxy (4HT); 4-oxo-2,2,6,6-tetramethyl-piperidinyloxy; 4-dimethylamino-2,2,6,6-tetramethyl-piperidinyloxy; 4-amino-2,2,6,6-tetramethyl-piperidinyloxy; 4-ethanoloxy-2,2,6,6-tetramethyl-piperidinyloxy; 2,2,5,5-tetramethyl-pyrrolidinyloxy; amino-2,2,5,5-tetramethyl-pyrrolidinyloxy; 2,2,5,5-tetramethyl-1-oxa-3-azacyclopentyl-3-oxy; 2,2,5,5-tetramethyl-3-pyrrolinyl-1-oxy-3-carboxylic acid; 2,2,3,3,5,5,6,6-octamethyl-1,4-diazacyclohexyl-1,4-dioxy; salts of nitrosophenolate; 2-nitrosophenol; 4-nitrosophenol; phenothiazine (PTZ); 3-oxophenothiazine; 5-oxophenothiazine; phenothiazine dimer; 1,4-benzenediamine; N-(1,4-dimethylpentyl)-N'-phenyl-1,4-benzenediamine; N-(1,3-(dimethylbutyl)-N'-phenyl-1,4-benzenediamine; N-nitrosophenyl hydroxylamine and salts thereof; nitrosobenzene; p-benzoquinone; nitrobenzene; nitrosobutane; n-nitrosodiphenylamine; diphenylphenylenediamine; nitrosocarbazole; 1-nitroso-2-naphthol; 2,4 dinitrobenzene; triphenyl phosphine; triethyl phosphine; tributyl phosphine; triphenyl phosphite; triethyl phosphite; tri-i-propylphosphite; tributyl phosphite; tricyclohexyl phosphite; sodium bisulfite; butyl mercaptan; dodecyl mercaptan; N,N-diethylhydroxylamine; N-benzoyl-N-phenylhydroxylamine; benzothiazol-2-yl-thiohydroxylamine; (benzyloxycarbonyl) hydroxylamine monoethanolamine; 4-phenylenediamine; 3-phenylenediamine; 4-aminodiphenylamine; diphenylamine; di-4-tolylamine; 4-nitrophenylamine; tert-butylamine; dibenzylamine, acetone oxime; phenyl N-t-butylnitrone; (4-pyridyl-N-oxide)-N-tert-butylnitrone; isomers thereof; mixtures of two or more thereof. The inhibitor(s) may be used alone or combined with a suitable diluent. Preferred other inhibitor compounds include hydroquinone (HQ); 4-methoxyphenol (MEHQ); 4-ethoxyphenol; 4-propoxyphenol; 4-butoxyphenol; 4-heptoxyphenol.

In one embodiment the polymerizable compound with at least one conjugated unsaturated group is acrylic acid, methacrylic acid and esters thereof which are particularly liable to polymerize among vinyl compounds. Said compounds may be present alone or as mixtures. Examples of the acrylic ester include methyl acrylate, ethyl acrylate, butyl acrylate, 2-ethylhexyl acrylate, 2-hydroxyethyl acrylate, and 2-hydroxypropyl acrylate, 2-[2-(2-ethoxyethoxy)ethoxy]ethyl acrylate, 1-octadecyl acrylate (stearyl acrylate), 1-hexadecyl acrylate (palmityl acrylate). Examples of the methacrylic ester include methyl methacrylate, butyl methacrylate, 2-hydroxyethyl methacrylate, and 2-hydroxypropyl methacrylate, 2-[2-(2-ethoxyethoxy)ethoxy]ethyl methacrylate, 1-octadecyl methacrylate (stearyl methacrylate), 1-hexadecyl methycrylate (palmityl methacrylate). Preferred methacrylic ester include 2-[2-(2-ethoxyethoxy)ethoxy]ethyl methacrylate, 1-octadecyl methacrylate (stearyl methacrylate), 1-hexadecyl methacrylate (palmityl methacrylate).

The inhibitors described herein are in particular suitable to stabilize 2-[2-(2-ethoxyethoxy)ethoxy]ethyl methacrylate, 1-octadecyl methacrylate (stearyl methacrylate), 1-hexadecyl methacrylate (palmityl methacrylate).

In one embodiment of the present invention an aliphatic alcohol with one to eight carbon atoms, preferably one to six, more preferably one to three carbon atoms, in particular methanol, 1-ethanol and 1-propanol, is added to the inhibitor and/or the polymerizable compound. Surprisingly it has been found that this addition accelerates dissolution of the inhibitor according to the present invention (i.e. either the in situ formed inhibitor or the novel inhibitor as described herein) while, after removal of the alcohol, stabilizes the solubility of the inhibitor in a given polymerizable compound. While the acceleration of the dissolution may be explained by kinetic factors it is completely surprising that a higher stability of the solubility of the inhibitor (i.e. a prevention of precipitation of inhibitor from the polymerizable compound) is achieved after removal of the alcohol, for example by distillation.

The inhibitors described herein may be prepared according to WO2007056439 and according to Singh, R. and Flowers, R. A. Chem. Commun., 2010, 46, 276-278.

Depending on the azine dye-based compound two different methods of preparation of the inhibitor may be contemplated.

In one embodiment of the present invention the inhibitor is prepared using a commercially available sulfonate salt. Said method comprises the steps of mixing a salt of the azine dye-based compound with a sulfonate salt in water, adding a water-immiscible solvent to obtain a mixture, heating the mixture to reflux for up to 24 hours, separating the water and the organic solvent phase to obtain the organic solvent phase, removing the organic solvent to obtain the inhibitor.

In a further embodiment of the present invention the inhibitor is prepared using a synthesized sulfonate salt. Said sulfonate salt may prepared by known methods, such as a method comprising the steps of contacting a phenolic compound with a base in an organic solvent to obtain a mixture, adding a sulfone to the mixture, stirring the mixture for up to 12 hours at room temperature, precipitating with organic solvent to obtain a sulfonate salt. The obtained sulfonate salt is then reacted with a salt of the azine dye-based compound as described above to obtain the desired inhibitor.

Examples of useful sulfones include 1,2-ethansulfone, 1,3-propanesulfone, 1,4-butanesulfon, 1,3-propanesulfone is particularly useful.

Useful bases include sodium hydride and calcium hydride.

Examples of said organic solvent include methylene chloride, chloroform, THF, diethylether, methyl tertbutyl ether.

Examples of useful phenolic compounds include hydroquinone (HQ), 4-methoxyphenol (MEHQ), 4-ethoxyphenol, 4-propoxyphenol, 4-butoxyphenol, 1,2-dihydroxybenzene, 2-methoxyphenol; 2,5-dichlorohydroquinone; 2,5-di-tert-butylhydroquinone (DBQH), acetylhydroquinone; 2,5-di-tert-butylhydroquinone is particularly useful.

The salt of the azine dye-based compound comprises the azine dye-based cation component as defined above and the anion component comprising at least one halide selected from the group consisting of $Cl^-$ (chloride), $Br^-$ (bromide), $I^-$ (iodide) and $F^-$ (fluoride).

The sulfonate salt comprises a $RSO_3-$ (sulfonate) anion component as defined above and at least one cation component selected from the group consisting of $Na^+$ (sodium), $K^+$ (potassium), $Li^+$ (lithium) and $NH_4^+$ (ammonium).

As indicated herein, the inhibitor to be employed in accordance with the present invention may either be an inhibitor formed in situ or an inhibitor formed prior to its use. In the latter case, a particularly preferred inhibitor is an inhibitor having the general formula ADX. These novel inhibitors preferably show anions with long chain aliphatic sulfonate residues, typically selected among straight chain aliphatic residues. Other suitable sulfonates are residues wherein the aliphatic moiety of a sulfonate anion is substituted with a residue consisting a hydroxyl-substituted aromatic group, preferably corresponding to an inhibitor known in the art. A particular preferred embodiment of such a novel inhibitor in accordance with the present invention is the sulfonate of formula I-4 as described herein.

According to the present invention a method of purification of a polymerizable compound with at least one conjugated unsaturated group may comprise the steps of contacting the polymerizable compound with either a preformed inhibitor, or the mixture of the azine dye-based compound and the sulfonate compound, to obtain a mixture, heating the mixture, and distilling to obtain the purified polymerizable compound.

The method of purification of a polymerizable compound with at least one conjugated unsaturated group may comprise further the step of adding a second polymerization inhibitor selected among the known inhibitors illustrated above, preferably selected from the group consisting of hydroquinone (HQ), 4-methoxyphenol (MEHQ), 4-ethoxyphenol, 4-propoxyphenol, 4-butoxyphenol and 4-heptoxyphenol prior the heating step.

The distillation processes for purification polymerizable compounds as identified herein are carried out using conventional equipment and process parameters known to the average skilled person. Depending on the chemical nature of the polymerizable compounds, the boiling points and therefore required temperatures may be up to several 100° C. at ambient pressure. In order to reduce thermal stress, typically distillation processes therefore are carried out at reduced pressures, such as from 0.01 to 1 mbar, preferably 0.1 to 0.5 mbar, or from 0.2 to 0.4 mbar. The required temperatures when working at such reduced pressures typically in the range of from 100 to 300° C., with embodiments being from 150 to 250° C. etc. The inhibitors disclosed herein typically do show, as outlined before, satisfactory inhibitory activity at these temperatures. However, as also outlined herein, it may be required under particular circumstances to employ mixtures of inhibitors, adding in particular inhibitors which do display inhibitory activity at rather low temperatures, such as from 50 to 150° C. in order to provide the most preferred inhibitory activity.

In another embodiment of the present invention the method of purification of a polymerizable compound with at least one conjugated unsaturated group comprises further contacting the inhibitor as described herein with an alcoholic solvent, preferably in admixture with the polymerizable compound prior to the purification. More preferably the alcoholic solvent is removed prior to any subsequent reaction (purification, synthesis etc.), however, after the inhibitor has been completely dissolved.

Accordingly, the present invention further provides a possibility to improve the efficacy of the inhibitory activity. Accordingly, in one aspect, the present invention also provides a method of improving the efficacy of an inhibitor based on an azine-based compound as defined herein, characterized in that the improvement involves the provision of a minor amount of an aliphatic alcohol to dissolve the inhibitor (preferably in a quantity of the polymerizable compound), followed by employing such a solution during a process where the inhibitory activity is desired. In this aspect of the present invention, it furthermore has been found that it is possible to remove the aliphatic alcohol after having dissolved the inhibitor, without detrimental effect on solubility and/or inhibitory effect.

In accordance with the present invention, the principles described above in the context of a purification process by distillation may also be employed during synthetic processes used for the preparation of a polymerizable compound with at least one conjugated unsaturated group. Surprisingly, it has been found that the provision of an inhibitor, either in situ or as isolated inhibitor in accordance with the above disclosure also provides an inhibitory effect during the synthesis of polymerizable compounds, without interfering with the synthetic process. Thereby, the production of undesired side products including partially polymerized products during the synthesis may be prevented, thereby increasing the overall yield of the synthetic process while also facilitating the synthetic process, as less side products have to be separated from the desired final product. The prevention of undesired polymerization in particular prevents the formation of high molecular weight (oligomeric or polymeric) side products which potentially can yield undesired precipitates during the synthetic process, which in turn can damage the equipment employed (by clogging lines, by providing undesired coatings on inner surfaces of reaction vessels, which in turn may then give rise to additional problems in relation to thermal transfer etc.).

In accordance with the present invention, it is therefore possible to synthesize a polymerizable compound while using the above-identified in situ generation of the inhibitor in order to prevent undesired polymerization.

In one embodiment of the present invention the method of preparation of a polymerizable compound with at least one conjugated unsaturated group comprises the step of contacting the reaction mixture with either an isolated inhibitor or the mixture of the azine dye-based compound and the sulfonate compound as described above. As typical synthetic processes for the preparation of polymerizable compounds, such as those exemplified above, comprise reaction at elevated temperatures, an in situ formation as well as a required dissolution is achieved so as to provide the desired inhibitory effect.

The method of preparation of the polymerizable compound is in a particular embodiment of the present invention a transesterification reaction of an acrylic or a methaclyic ester with an alcohol in the presence of the inhibitor as described herein.

Suitable reaction parameters as well as catalysts suitable therefore are known to the skilled person. The transesterification reaction of said acrylic or a methaclyic ester may be carried out in the presence of a catalyst. The temperature may be 90° C. to 120° C., preferably at 100° C. to 110° C., and the reaction time may be 1 to 6 hours, preferably 2 to 4 hours.

Suitable transesterification catalysts are known to the average skilled person. Exemplary catalysts are for example disclosed in WO 2011/157645 A2 as well as in U.S. Pat. No. 4,983,761. These documents also disclose examples of suitable reaction conditions for transesterification reactions.

Examples of the alcohol suitable for the transesterification include ethanol, butanol, 2-ethylhexanol, 2-hydroxyethanol, and 2-hydroxypropanol, 2-[2-(2-ethoxyethoxy)ethoxy]ethanol, 1-octadecanol (stearyl alcohol), 1-hexadecanol (palmityl alcohol). Preferred alcohols include 2-[2-(2-ethoxyethoxy)ethoxy]ethanol, 1-octadecanol (stearyl alcohol), 1-hexadecanol (palmityl alcohol). Said alcohols may be present alone or as mixtures.

Examples of said acrylic and methacrylic esters include in particular $C_1$-$C_6$ acrylates and $C_1$-$C_6$ methacrylates, preferably methyl, ethyl, propyl or butyl acrylates and methacrylates.

The present invention will be further illustrated by the following examples.

EXAMPLES

Preparation of Inhibitors

The compounds I-1 and I-2 are prepared and isolated according to WO2007056439.

Methylene blue and sodium alkyl sulfonate are dissolved in water and heated to reflux in the presence of water-immiscible dichloromethane. The organic phase is subsequently separated, washed, dried, filtered and concentrated to give the methylene blue alkyl sulfonate salt.

The compounds I-1a to I-3a are prepared in situ.

The compound I-4 is prepared using a two-step procedure. First the phenolic inhibitor 2,5-di-tert-butylhydroquinone (DBHQ) is reacted with 1,3-propanesultone to yield a sulfonic acid sodium salt (see Singh, R. and Flowers, R. A. Chem. Commun., 2010, 46, 276-278). Next anion exchange with methylene blue is performed and the new salt is isolated by extraction.

The compounds are summarized in Table 1.

TABLE 1

| Inhibitor | Salt 1 | Salt 2 | Isolated/In situ generation |
|---|---|---|---|
| I-1 | sodium 1-octanesulfonate | methylene blue | isolated |
| I-2 | sodium 1-hexadecanesulfonate | methylene blue | isolated |
| I-3 | sodium 1-dodecanesulfonate | methylene blue | isolated |
| I-1a | sodium 1-octanesulfonate | methylene blue | in situ |
| I-2a | sodium 1-hexadecanesulfonate | methylene blue | in situ |

TABLE 1-continued

| Inhibitor | Salt 1 | Salt 2 | Isolated/ In situ generation |
|---|---|---|---|
| I-3a | sodium 1-dodecanesulfonate | methylene blue | in situ |
| I-4 | sodium 3-(2,5-di-tert-butyl-4-hydroxy-phenoxy)-propane-1-sulfonate | methylene blue | isolated |

Example 1

The compound I-1 is prepared by heating 1 g (3.13 mmol) of methylene blue chloride and 0.675 g (3.13 mmol) of sodium 1-octanesulfonate at reflux for 24 h in 100 mL of $CH_2Cl_2$ and 10 mL of water. The layers are separated, and the organic phase is washed with water (3×10 mL) and dried over magnesium sulfate. Filtration and concentration gave 1.49 g (75%) of the octanesulfonate salt of methylene blue.

Example 2

The compounds I-1a to I-3a are prepared in situ (by mixing the starting components with a polymerizable compound, see below). As pre-treatment a 1:1 molar mixture of the constituent salts was finely ground. This is done to homogenize the mixture and to provide intimate contact between both salts.

Example 3

The compound I-4 is prepared by deprotonation of 1 g of 2,5-di-tert-butylhydroquinone (DBHQ) (4.50 mmol) in the presence of 0.13 g sodium hydride (5.40 mmol) in 20 mL THF at room temperature. The reaction mixture was stirred at room temperature for 15 minutes, then 0.55 g of 1,3-propanesultone (4.50 mmol) is added slowly and the reaction mixture is stirred overnight. The excess sodium hydride is quenched by slow addition of methanol. Precipitation with $Et_2O$ followed by filtration and washing with $Et_2O$ yields 1.57 g of a white solid (95%). Anion exchange with methylene blue is performed as described above via extraction from water with dichloromethane.

Example 4

Visual Assessment of the Inhibitors in Stearyl Methacrylate (SMA)

The solubility of the compounds in SMA is assessed visually. An intense blue/purple color of the liquid phase and the absence of small solid particles indicate good solubility. Vice versa, the lack of an intense color or the presence of particulates, are indications of poor inhibitor solubility. Samples are prepared by adding a known amount of the inhibitor (100 ppm in each case) to 10 g SMA. This mixture is then sonicated, to break down larger particles, and brought to the measuring temperature using a water bath. The results are summarized in the Table 2.

TABLE 2

| Inhibitor | Temperature (° C.) | Solubility |
|---|---|---|
| MB | 25 | poor |
| MB | 50 | Poor |
| I-1a | 25 | Partial |
| I-1a | 50 | Good |

TABLE 2-continued

| Inhibitor | Temperature (° C.) | Solubility |
|---|---|---|
| I-3a | 25 | Poor |
| I-3a | 50 | Partial |
| I-2a | 25 | Poor |
| I-2a | 50 | Partial |
| I-1 | 25 | Partial |
| I-1 | 50 | Good |
| I-4 | 25 | Partial |
| I-4 | 50 | Good |

Example 5

To improve solubility of inhibitors, I-2a, I-4 and MB are first dissolved in 0.1 ml of methanol per mg of inhibitor. SMA is then added to this methanolic solution. This results in a very intense blue solution with no visible particles. Next, the methanol is removed under reduced pressure on the rotavapor (45° C., 1 mbar, 30 minutes). Upon standing, two different outcomes were observed (FIG. 1, left picture). The right vial contains 250 ppm of MB in SMA.

Two different phases can be seen; a liquid phase and a solid phase at the bottom which contains inhibitor particles as well as some precipitated SMA. The vial on the left contains 250 ppm of MB and 250 ppm of sodium 1-hexadecanesulfonate in SMA. Clearly no phase separation is occurred; no inhibitor particles can be seen and no SMA is precipitated. On removal of methanol and cooling, methylene blue is precipitating, while the inhibitor according to the present invention stays in solution.

A similar approach is used to improve the solubility of I-4. This leads to an increase in color intensity (FIG. 2).

Accordingly the solubility can be increased by mixing a methanol solution of the inhibitor with SMA followed by removal of the methanol. The resulting solution is thermodynamically stable in the presence of the alkylsulfonate component. In the absence of such a component the methylene blue precipitates.

Example 6

Purification of SMA in the Presence of the Inhibitors

The inhibitory effect of the compounds during purification of SMA by performing a kugelrohr distillation on a 10 g SMA sample is summarized in Table 3. The temperature of the kugelrohr is set to 240° C. The distillation starts when the vacuum reached about 0.2 mbar. Polymerization in the rotating pitch is evaluated by visually determining increased viscosity.

TABLE 3

| Inhibitor | Concentration (ppm) | Polymerization | Yield (%) |
|---|---|---|---|
| I-1a | 500 | no | 92 |
| I-2a | 500 | no | 95 |
| I-4 | 500 | no | 94 |
| I-1 | 500 | no | 93 |

In all cases temperatures of 220-240° C. are needed to completely dissolve the inhibitors. The inhibitors were added as such to the SMA prior to the distillation, no methanolic solution as described earlier is used.

SMA could be distilled with the Kugelrohr with these inhibitors without significant polymerization.

Example 7

Synthesis of SMA in the Presence of the Inhibitors

SMA is prepared via transesterification in the presence of the indicated inhibitors. A two-neck flask, equipped with a Dean-Stark apparatus and a reflux condenser, is charged with three equivalents of methyl methacrylate, one equivalent of stearyl/palmityl alcohol and 500 ppm of inhibitor. Air is bubbled through the solution using a needle, septum and vacuum pump, set at 900 mbar. The temperature of the oil bath is set at 105° C. Once the fatty alcohol has molten and the temperature of the solution doesn't increase anymore, 1.25 mol % of a transesterification catalyst is added to the reaction mixture.

The methyl methacrylate/methanol azeotrope is collected and at the end of the reaction any remaining methyl methacrylate is removed under reduced pressure at the rotavapor.

Table 4 gives an overview of the performed reactions. The color of the reaction mixture and the solubility of the catalyst/inhibitor at the start and at the end of the reaction are also indicated.

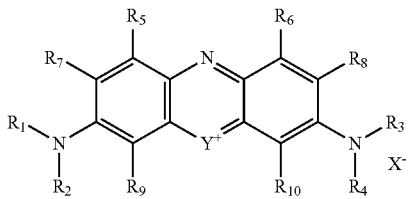

wherein:
Y is S.
$R_1$-$R_4$ is methyl,
$R_5$-$R_{10}$ is hydrogen and

TABLE 4

| Reaction | Inhibitor | Scale | Properties start | Properties end |
| --- | --- | --- | --- | --- |
| E | 500 ppm MeHQ | 82.6 g alcohol | colorless solution | yellow liquid white |
|  |  | 0.322 mol | homogeneous | precipitate (catalyst) |
| F | 500 ppm MB | 82.6 g alcohol | dark blue solution | brown liquid |
|  |  | 0.322 mol | homogeneous | black precipitate |
| G | 500 ppm MB | 82.6 g alcohol | dark blue solution | brown liquid very |
|  | 500 ppm CH$_3$(CH$_2$)$_{15}$SO$_3$Na | 0.322 mol | homogeneous | little precipitation |
| H | 500 ppm I-4 | 82.6 g alcohol | deep purple solution | purple liquid |
|  |  | 0.322 mol | homogeneous | black precipitate |

All starting mixtures are homogeneous; catalyst and inhibitors dissolve well in the alcoholic medium. However, at the end of the reaction, after removal of methanol and excess of methyl methacrylate, the polarity of the medium is changed dramatically. Small black particles can be observed when pure methylene blue or I-4 are used as inhibitor (reactions F and H). The addition of sodium 1-hexadecanesulfonate to methylene blue (reaction G) renders the inhibitor more soluble and much less particles are seen. The color of the reaction mixture changed from blue to brown in reaction (F and G) where methylene blue or methylene blue in combination with the sodium 1-hexadecanesulfonate was used. The reaction (H) with the mixed inhibitor I-4 retains a purple color after reaction.

As can be seen from the FIG. 3, while the type of inhibitor does not have a big influence on the kinetics; as nearly full conversion is achieved within three hours, the overall evaluation of the reactions indicates that with inhibitors in accordance with the present invention better results are obtained (less precipitation and/or better purity/less side products). No polymerization is observed during the reactions.

SMA was successfully prepared from methyl methacrylate and the fatty alcohol in presence of the inhibitors. Full conversion could be obtained in three hours. No polymerization is observed with any of the described inhibitors. After reaction and removal of excess methyl methacrylate, methylene blue tended to precipitate. With addition of an alkylsulfonate component (i.e. working in accordance with the present invention) much less particles are observed.

The invention claimed is:
1. An azine dye-based compound having the general formula (ADX):

X$^-$ is any anion selected from the group consisting of CH$_3$(CH$_2$)$_n$SO$_3^-$, with n being an integer of from 6 to 30, or an organic sulfonate comprising an hydroxyl substituted aromatic moiety.

2. The azine dye-based compound according to claim 1, wherein n is an integer of from 7 to 20.

3. The azine dye-based compound according to claim 2, wherein X$^-$ is selected from any of CH$_3$(CH$_2$)$_7$SO$_3^-$, CH$_3$(CH$_2$)$_{15}$SO$_3^-$, or CH$_3$(CH$_2$)$_{11}$SO$_3^-$.

4. The azine dye-based compound according to claim 1, wherein the organic sulfonate comprising an hydroxyl substituted aromatic moiety is 3-(2,5-di-tert-butyl-4-hydroxyphenoxy)-propane-1-sulfonate.

5. A composition comprising a polymerizable compound with at least one conjugated unsaturated group and an azine dye-based compound according to claim 1.

6. The composition according to claim 5, wherein the azine dye-based compound is present in a concentration of 10 to 1000 ppm.

7. The composition according to claims 5, wherein the polymerizable compound with at least one conjugated unsaturated group is selected from acrylic acid, methacrylic acid and esters thereof.

* * * * *